United States Patent [19]

Passell et al.

[11] Patent Number: 4,472,354
[45] Date of Patent: Sep. 18, 1984

[54] SYSTEM FOR CONTINUOUSLY MONITORING THE IONIC CONTENT OF STEAM-PRODUCING WATER

[75] Inventors: Thomas O. Passell, Palo Alto; Michel N. Robles, Livermore; James L. Simpson; Constantine N. Spalaris, both of San Jose, all of Calif.

[73] Assignee: Electric Power Research Institute, Inc., Palo Alto, Calif.

[21] Appl. No.: 385,814

[22] Filed: Jun. 7, 1982

Related U.S. Application Data

[62] Division of Ser. No. 199,247, Oct. 21, 1980, abandoned.

[51] Int. Cl.³ .................. G01N 31/08; G01N 31/04
[52] U.S. Cl. .................................. 422/62; 73/23.1; 210/298; 210/662; 422/70; 422/81; 436/38; 436/52; 436/161
[58] Field of Search ............... 422/62, 70, 81; 436/38, 436/52, 161; 210/662, 298.2; 73/23.1; 364/499, 500

[56] References Cited

U.S. PATENT DOCUMENTS

| | | | |
|---|---|---|---|
| 3,676,649 | 7/1972 | Burk | 73/23.1 |
| 3,897,213 | 7/1975 | Stevens et al. | 422/81 |
| 4,229,971 | 10/1980 | Ririe, Jr. | 436/161 |

OTHER PUBLICATIONS

Peterson et al.—Steam-Purity Monitoring for Turbine Corrosion Control—A Total Plant Survey 40IWC Oct. 1979.

Primary Examiner—Michael S. Marcus
Attorney, Agent, or Firm—Flehr, Hohbach, Test, Albritton & Herbert

[57] ABSTRACT

An on-line and continuous sampling system for monitoring the ionic content of steam-producing water in a steam-operated electrical power plant. The monitoring system comprises a plurality of sampling lines and associated apparatus for sampling the steam-producing water at a number of different points in the power plant, an ion chromatographic subsystem for analyzing the sampled water, a calibration subsystem for calibrating the ion chromatographic subsystem, and an automatic control subsystem for operating the monitoring system of the present invention.

15 Claims, 4 Drawing Figures

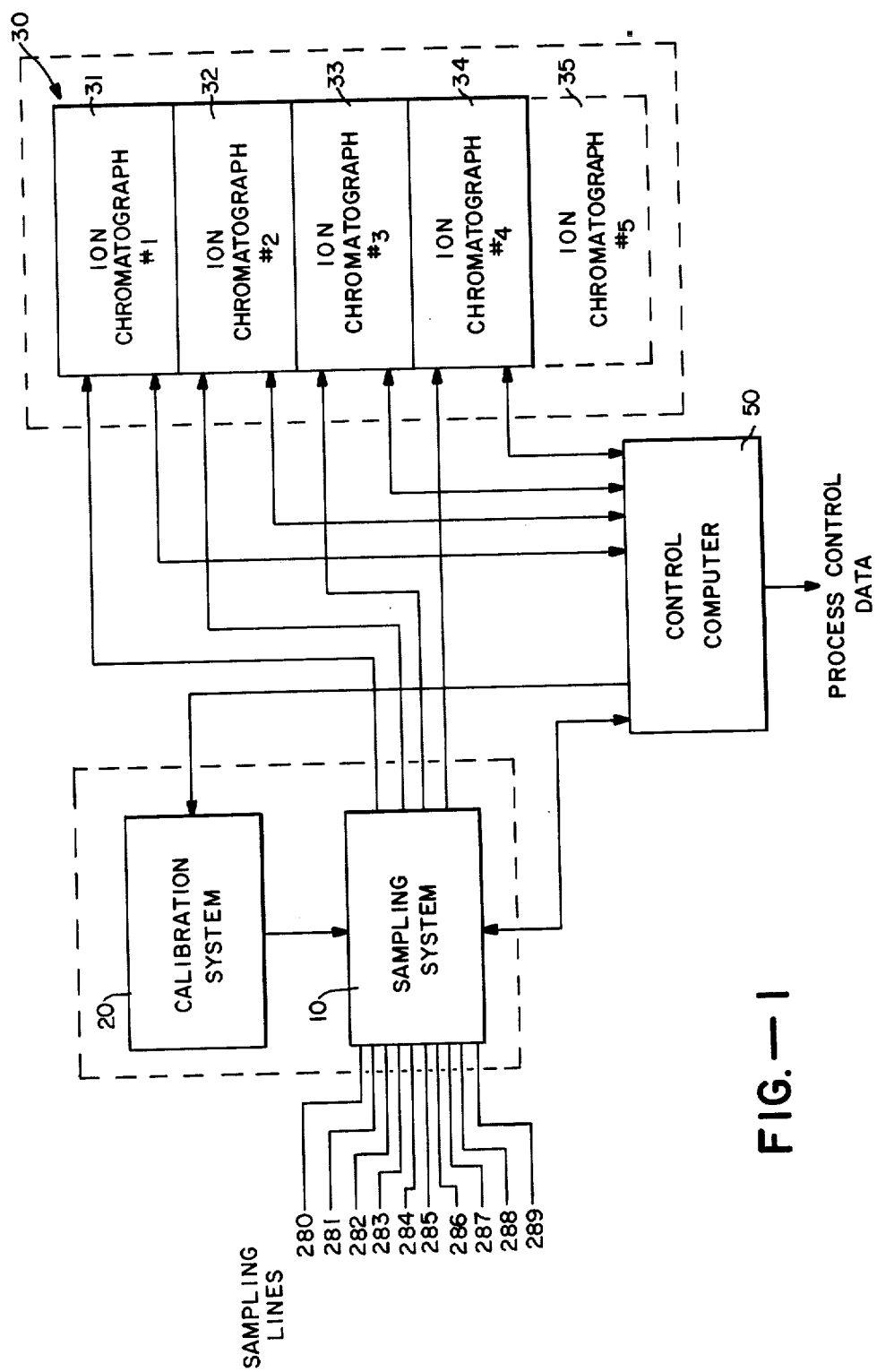
FIG.—1

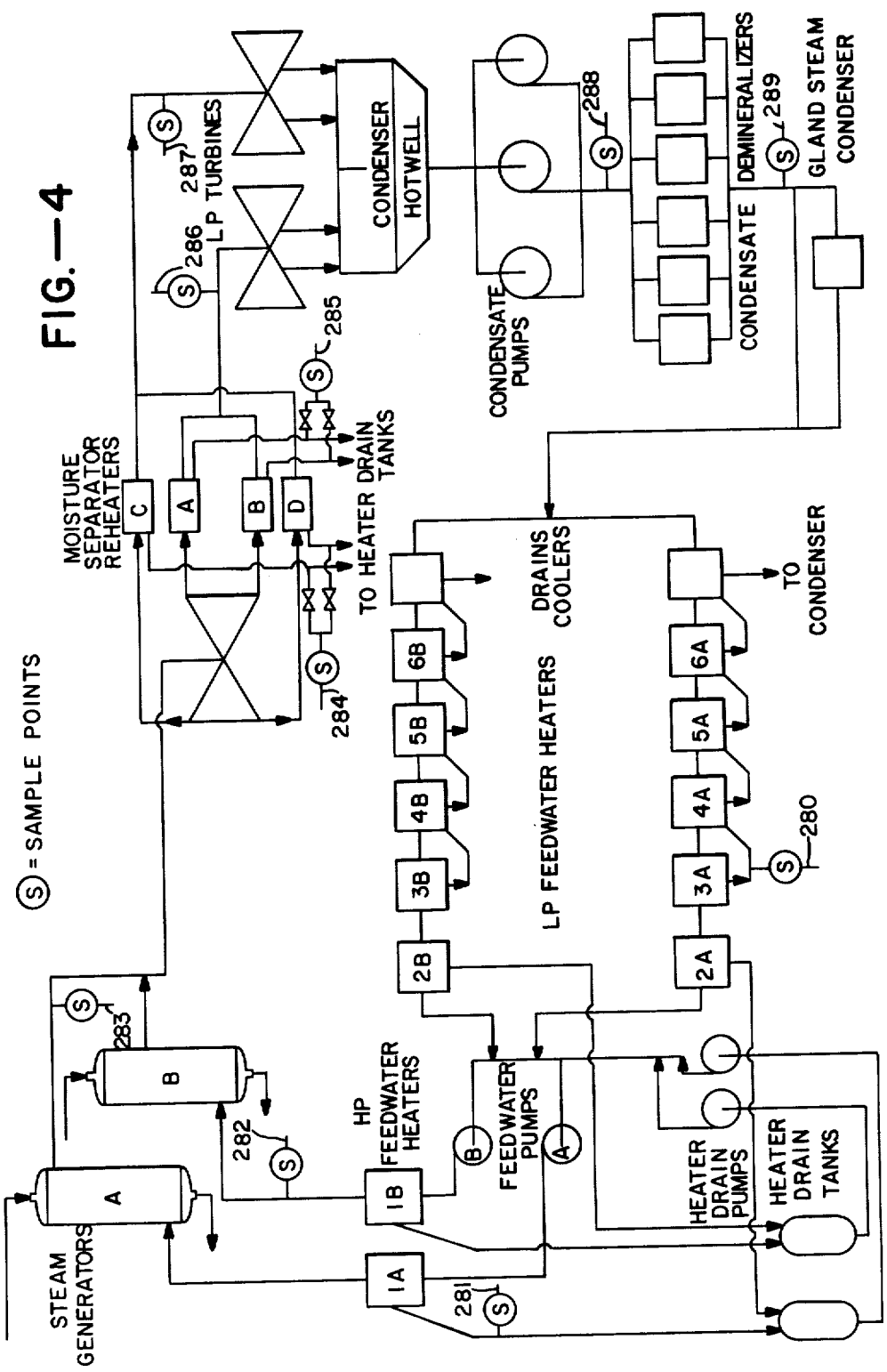
FIG.—4

SYSTEM FOR CONTINUOUSLY MONITORING THE IONIC CONTENT OF STEAM-PRODUCING WATER

This is a division of application Ser. No. 199,247 filed Oct. 21, 1980, abandoned.

The present invention relates generally to systems for monitoring steam-purity in steam operated electrical power plants, and more particularly to a system for continuously monitoring the ionic content of steam-producing water flowing in an electrical power plant.

Corrosive impurities, such as chloride ($Cl^-$) and sodium ($Na^+$), present in the steam-producing water of steam-generating power plants are a major problem in the electrical power industry. The level of concentation of these impurities is increased when the steam-producing water is vaprozied and converted to steam. As such, the impurities tend to accumulate in the plant's steam turbines and steam generators. An accumulation of these impurities will eventually cause equipment failures. The problem has been experienced in units that vary in type from low-pressure turbines operating at a pressure of 1000 psig to units with super-critical one-through steam generators.

In an attempt to eliminate the problem, guidelines have been established as to recommended levels of steam purity. Power plant operators have accordingly had to develop new instrumentation and procedures for monitoring steam purity to assure operation within the recommended guidelines.

For example, a continuous analyzer has been developed to continuously monitor sodium, dissolved oxygen, pH, cation conductivity, and the specific conductivity of the steam flowing in the plant steam/water cycle. The continuous analyzer includes a sampling nozzle, a cooler/condenser, thermocouples to measure steam and condensate temperatures, monitors for sodium, dissolved oxygen, pH, cation and specific conductivity, a multi-point recorder, and a sample flow control system. The continuous analyzer system also includes a grab sampling program involving ion chromatographic analysis for the detection of certain anions and cations. The grab sampling program involves the taking of samples at different points in the plant by manually opening a spigot in the piping to collect the fluid flowing in the piping in a container. In the case of steam, the steam is first cooled to its liquid state before it enters the container. The fluid in the container is then analyzed in an ion chromatograph to detect for the presence of certain ions. See S. H. Peterson, J. C. Bellows, D. F. Pensenstadler, and W. M. Hickman "Steam Purity Monitoring for Turbine Corrosion Control: A Total Plant Survey," paper given at the 40th International Water Conference, 1979.

Grab sampling programs like the one described above, however, are unsatisfactory for a number of reasons. First, as the ions to be detected are present in extremely small concentrations—on the order of one part-per-billion for sodium ($Na^+$)—contamination of the container is always a problem. For example, sodium ions may be present in the container prior to sampling because the person doing the sampling touched the inside of the container. Second, in grab sampling programs, samples are taken periodically as opposed to continuously; thus, large transients in the concentration levels between grabs may be missed. Third, grab sampling usually changes the flow rate of the fluid in the piping being sampled which can cause artificial transients in the concentration levels of the ions being monitored. Finally, the individuals taking the grab samples will each tend to do it differently which can produce major differences in the concentration levels measured for any given grab sample.

The present invention is directed to an improved system for continuously monitoring the ionic content of steam-producing water in a steam-operated electrical generating power plant. The system of the present invention uses ion chromatographic analysis to monitor inorganic anions, monovalent cations, divalent cations, and anions of organic acids. The system is able to detect these ionic impurities in the sub part-per-billion to part-per-million range of concentrations. By sampling the steam-producing water—in both its liquid and vapor state—at a multiple number of points in the plant steam/water cycle, the system of the present invention provides an ion profile of the steam-producing water. This gives an indication of the extent of corrosive impurities in the water. The system has none of the disadvantages inherent in a grab sampling program. The system gives a more precise and improved assessment of steam purity than heretofore accomplished.

An object of the present invention is to provide an automatic and continuously-operating system for monitoring the chemical ionic content of steam-producing water at various points in the plant steam/water cycle.

The monitoring system of the present invention includes means for on-line and continuous sampling of the steam-producing water at different points in the power plant. Ion chromatographic means are provided and are connectable in fluid communication with the sampling means for detecting for the presence of corrosive impurities in the steam-producing water at the different sample points. Calibration means are also provided for calibrating the ion chromatographic means. An automatic control means controls the operation of the system.

In a preferred embodiment, the ion chromatographic means comprises four ion chromatographs, each for monitoring a different ion. Particularly, the ion chromatographs will monitor for inorganic anions, monovalent cations, divalent cations, and anions of organic acids. The sampling means of the present invention provides samples of the steam-producing water over a selected period of time and at a multiple number of points in the plant steam/water cycle. The system thus provides an ion profile of the steam-producing water flowing in the plant over a selected period of time. Preferably, the system will sample the steam-producing water in both its liquid and vapor states.

The monitoring system of the present invention will be described in more detail hereinafter in conjunction with the drawings wherein:

FIG. 1 is a functional block diagram of the monitoring system of the present invention;

FIG. 4 is a schematic diagram of the plant steam/water cycle of a pressure water reactor once-through steam generator illustrating the location of the sample lines.

Figures 2, 3:
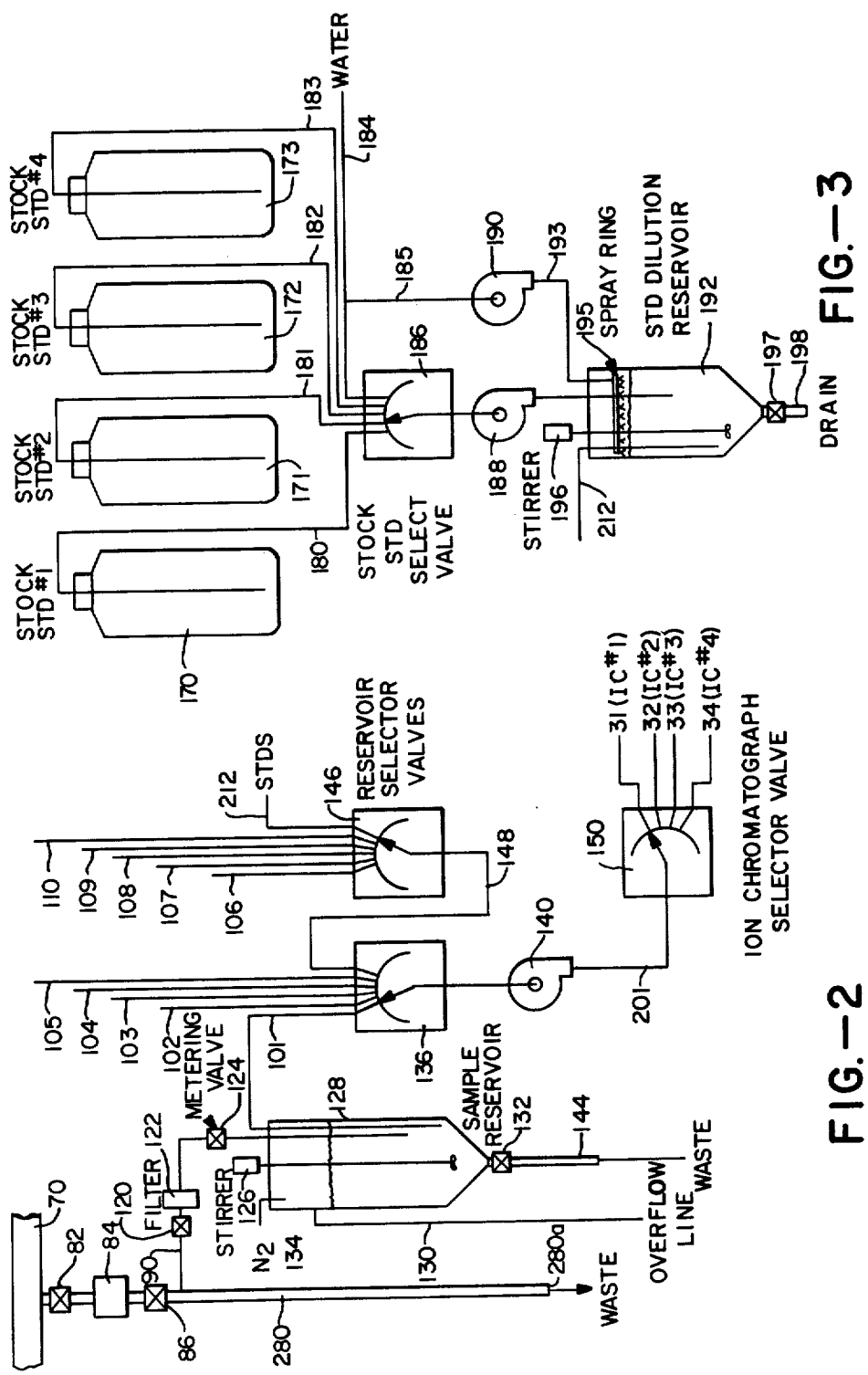
FIG. 2 is a schematic diagram that illustrates the sampling subsystem of the present invention.
FIG. 3 is a schematic diagram that illustrates the calibration subsystem of the present invention.

Referring now to the drawings, FIG. 1 is a functional block diagram of the monitoring system of the present invention for monitoring the ionic content of steam-producing water in a steam-operated electrical generating power plant. The monitoring system includes a sampling subsystem 10, a calibration subsystem 20, and a ion chromatographic subsystem 30 that includes a plurality of ion chromatographs 31 through 34. The system also includes control means such as control computer 50 for automatically controlling the operation of the system and for data acquisition and processing.

The ion chromatographic subsystem will preferably be located in an air conditioned room to provide appropriate ambient temperature control. It will also be located in a centralized location to minimize the length of the runs of the sample lines, discussed below, of the sampling subsystem.

The arrangement of the apparatus of the sampling subsystem is shown in FIG. 2. As shown, a plurality of sampling lines are used to sample steam-producing water at different points in the steam-operated electrical power plant. In the embodiment illustrated, ten sampling lines 280 through 289, see FIGS. 1 and 4, are used to sample both steam and water at different points in the plant. By appropriately selecting the sampling points, the sources and sinks of each measured corrosive impurity may be identified. It is to be understood that the system of the present invention may be used in any type of steam-generating electrical power plant, whether fossil or nuclear fueled, and that any number of sampling lines deemed operably desirable may be used. Also the location of the sample points in the plant may be varied as desired.

In FIG. 2, the apparatus for only one sample line 280 is shown, as the apparatus for and operation of the other sampling lines are substantially the same. As shown, sample line 280 is interfaced with the steam-producing water flowing in the power plant through piping 70. A valve 82 for controlling the flow of water into the sample line is located at the interface. Flow rates through the sample line will be sufficient to provide a Reynolds number greater than 4000. A cooler 84 is provided to reduce the temperature of the sampled water in order to prevent damage to the ion chromatographs. The ion chromatographs should receive the sampled water at a temperature of between about 14° C. and 34° C. An inspection valve 86 is located in sample line 280 downstream of cooler 84. A cleaning agent for cleaning the sample line may be introduced through valve 86. The water in the sample line may also be checked for naturally absorbing layers of corrosion product oxide by means of valve 86.

The sampling lines of the present invention which are connected at points in the plant in which steam rather than water is flowing will also include suitable condenser means. The condenser means will be located between valve 82 and inspection valve 86 to convert the steam to water prior to its entry into sampling conduit 90. Sample lines 283, 286 and 287, see FIG. 4, will include such condenser means. In this sense, steam-producing water is being sampled in its vaporized state, but it is converted back to its liquid state before it enters conduit 90. The steam-producing water may be sampled in both its liquid state (water), as with sample line 280, and in its vapor state (steam), as with sample line 283. However, if it is sampled in its vapor state, it must be converted back to its liquid state for proper analysis in ion chromatographic subsystem 30. Thus, in referring to the sampling of steam-producing water, it is to be understood that steam-producing water may be sampled in its vapor and/or liquid state. But the steam-producing water must be in its liquid state for entry into the ion chromatograph subsystem.

By operation of flow-control valve 120, the sampled water in sample line 280, which may have an outside diameter of between ¼ and ⅜ of an inch, flows into sampling conduit 90, which may have an outside diameter of 3 millimeters. The sampled water that does not flow into conduit 90 flows out of the sample line at end 280a where it may be returned to the plant steam/water cycle.

After flowing through valve 120, the sampled water passes through filter 122 where any solids in the water are removed. This prevents solids from entering the chromatographic subsystem. A metering valve 124 meters the flow of sampled water through conduit 90 and into sample reservoir 128, which has a capacity of about 0.5 liter. The metering valve permits the reservoir to be slowly filled. An overflow line 130 is provided in case the reservoir is overfilled. In reservoir 128, the sampled water is covered with nitrogen ($N_2$) and mixed by means of a stirrer 126. The nitrogen is fed into the reservoir through line 134. By covering the sampled water with nitrogen, a change in its ionic content by exposure to oxygen in the air is prevented.

Over a predetermined period of time, which may be five to six hours and which is called the fill cycle, the steam-producing water flows through sample line 280 and into reservoir 128 via conduit 90. At the end of the fill cycle, stirrer 126 mixes the sampled water. The sampled water in the reservoir is then injected into each of the ion chromatographs in the ion chromatographic subsystem—each ion chromatograph detecting for the presence of selected ions.

By flowing steam-producing water into the reservoir over the period of the fill cycle, the system of the present invention provides sample averaging. That is, the system gives an average reading of the water's ionic content over the time period of the fill cycle, eliminating fluctuations that might otherwise occur.

The steam-producing water in reservoir 128 is injected into the ion chromatographs by means of constant volume metering pump 140. The sampled water flows from reservoir 128 via conduits 101 and 201 where it is directed by means of selector valve 150 to the selected ion chromatograph. By operating metering pump 140 for a precise period of time, the appropriate volume, usually one to ten milliliters, of sampled water is injected into each ion chromatograph.

After the appropriate amount of steam-producing water has been injected into each of the ion chromatographs, the reservoir will be emptied by means of drain valve 132 and drain line 144. A new reservoir-fill cycle may be initiated. Once the reservoir is filled, the water contained therein may again be selected for analysis in the ion chromatographic subsystem.

As illustrated, the steam-producing water contained in any of the ten sample reservoirs—one for each sample line—may be injected into any one of the four ion chromatographs. This is accomplished by appropriately operating reservoir selector valves 136 and 146, and ion chromatograph selector valve 150. Conduits 102 through 110 establish fluid communication between the other nine reservoirs of the present system and the reservoir selector valves. Although valves 136 and 146 are shown as separate valves connected by a conduit 148, it is to be understood that the reservoir selector valve may be a single valve.

In operation, each of the sample reservoirs of the system of the present invention are filled with steam-producing water over the period of the fill cycle. The water in the respective reservoirs is then selectively injected into each ion chromatograph. That is, after the steam-producing water flowing through sample line 80 has been analyzed, the steam-producing water of sample line 81 may be analyzed and so on for each sample line. This gives an ion profile of the steam-producing water around the plant steam/water cycle over the period of the fill cycle. At the end of the fill cycle, a new fill cycle may be initiated by again filling each reservoir with steam-producing water. Over the period of the fill cycles, the system provides continuous sampling of the steam-producing water.

As discussed heretofore, in a preferred embodiment, the ion chromatograph subsystem comprises four ion chromatographs 31 through 34 wherein each of the ion chromatographs are designed to detect for the presence of different ions. For instance, ion chromatograph 31 is used to detect inorganic anions such as fluoride ($F^-$), chloride ($Cl^-$), phosphate ($PO_4^-$), and sulphate ($SO_4^=$). With present ion chromatographic techniques, the detection limits for these anions are generally between about 1 and 5 parts-per-billion for a one milliliter injected sample. To further reduce detection limits, a concentrator column, as is known in the art, can be used with ion chromatograph 31. This allows a larger sample volume to be injected into the ion chromatograph.

In the preferred embodiment, ion chromatograph 32 will be used to detect for monovalent cations such as sodium ($Na^+$), potassium ($K^+$), ammonium ($NH_4^+$), and lithium ($Li^+$). Detection limits for these cations are typically less than one part-per-billion for a one milliliter injected sample. Concentrator columns may also be used here to reduce detection limits. However, conentrator columns are not effective when trying to concentrate a less tightly held minor ion in the presence of a major ion, for example, sodium in the present of a thousand times more ammonium, which is typical for pressure water reactors where ammonia is used for pH control. In this situation, the capacity of the concentrator column is exceeded and the sodium ion is partially eluted from the concentrator by the more tightly held ammonium ion. Therefore, a concentrator column cannot be used. In this case, to reduce detection limits, large volume sample injections may be made directly into the separator column.

Ion chromatograph 33 is used to detect the divalent cations of magnesium and calcium. These ions are analyzed with the same resin columns used in analyzing the monovalent cations. A different eluent, however, is used. The detection limit for these cations is about one nanogram per milliliter. A concentrator column may be used to lower detections limits. And here there is no problem with ammonium exhausting the concentrator's capacity, as the divalent cations are retained more strongly than the monovalent cations.

Ion chromatograph 34 may be used to detect the anions of organic acids, such as formic, acetic, and succinic acids. A concentrator column may also be used to lower detection levels.

In addition to monitoring the above-discussed corrosive impurities, the system of the present invention may be modified to detect other impurities. For example, one of the ion chromatographs may be modified, as is known in the art, to detect the anions of carbonates present in the steam-producing water. This could be done by coupling the well-known technique of ion chromatograph exclusion to one of the ion chromatographs to provide maximum information about the presence of carbonates. Or as shown in phantom in FIG. 1, ion chromatograph 35, which uses the ion chromatograph exclusion technique, may be added to the ion chromatographic subsystem so that the system can detect carbonates as well as inorganic anions, monovalent cations, divalent cations, and anions of organic acids.

Ion chromatographic subsystem 30 may also be modified by adding an ion chromatograph that is capable of detecting the anions of boric and sillicic acid. The subsystem may also be modified or expanded by adding a coulometric detector to an ion chromatograph to measure transition metal corrosion products, such as iron oxides. Thus, the system may be so inclusive as to be able to monitor inorganic anions, monovalent cations, divalent cations, anions of organic acids, anions of carbonates, anions of boric and sillicic acid, and transition metal corrosion products.

Now referring to FIG. 3, the arrangement of the apparatus of calibration subsystem 20 is shown. The calibration subsystem provides current calibration data and automatic updating of the ion chromatograph response factors. It includes apparatus for injecting various stock standard solutions into the various ion chromatographs. The stock standard solutions are stored in separate reservoirs 170 through 173 and are connected by respective conduits 180 through 183 to a selector valve 186. The respective stock standard solutions, as discussed below, are injected into the respective ion chromatographs to check the accuracy, as known in the art, of the chromatographic readings. For example, stock standard solution No. 2 in reservoir 171 would contain sodium in solution at a known concentration for use in verifying the readings of ion chromatograph 32, which detects for the presence of sodium and other monovalent cations.

Any one of the stock standard solutions may be transferred from its respective reservoir to a dilution reservoir 192 by means of a metering pump 188. The metering pump accurately meters the solution flowing into the dilution reservoir. Selector valve 186 selects the standard solution that is to be transferred to the dilution reservoir. In reservoir 192, the stock standard solution is diluted with ultrapure water (one micromho per centimeter). The ultrapure water flows into reservoir 192 through conduits 184, 185 and 193 by means of metering pump 190. The water is sprayed into the solution contained in the reservoir through a spray ring 195. A stirrer 196 mixes the solution and the water. The standard solutions have to be diluted as they are stored at relatively high concentrations. For example, the concentration for sodium in reservoir 171 would be on the order of 100 parts-per-billion. To calibrate ion chromatograph 32, the concentration of sodium would have to be decreased to about 10 parts-per-billion.

After mixing in the dilution reservoir, the solution in the reservoir is sampled for injection into the appropriate ion chromatograph. To this purpose, the diluted stock standard solutions flows through conduit 212 to select valve 146 where it is directed to the appropriate ion chromatograph by means of selector valve 150, see FIG. 1. Pump 140 is used to flow the standard solutions from the dilution reservoir to the appropriate ion chromatograph.

After the selected ion chromatograph has been calibrated, the dilution reservoir is emptied by means of drain valve 197 and conduit 198. It is then rinsed prior to the preparation of the next stock standard solution. Standardization of the ion chromatographs will be based on a frequency programmed into the control subsystem 50. Initial recalibration frequency will be once after the completion of every fill cycle in the sample subsystem. Replacement of the stock standard solutions will be at a minimum interval of every two weeks.

For automatic operation of the monitoring system of the present invention, control subsystem 50 is provided. Control subsystem 50 is a computer system that provides time-based control of the various valves, pumps and associated equipment of the monitoring system. Subsystem 50 operates the appropriate pumps and valves of the system to transfer the sampled water from the selected sample line to a selected ion chromatograph. It operates to transfer a selected stock standard solution to a selected ion chromatograph. Control subsystem 50 also provides for data acquisition from each ion chromatograph and the processing of such data. This data may be analyzed by a linear regression routine, that is, comparing the standard reading for one fill cycle to the reading for the next to determine if system response factors are changing.

Although the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A system for monitoring corrosive impurities in the steam-producing water of a steam-operated electrical power plant, comprising:
   a plurality of sample lines connected at different points in the power plant for on-line and continuous sampling of the steam-producing water at said different points;
   valve means in each of said sample lines for controlling the flow of steam-producing water therethrough;
   conduit means connected to each of said sample lines for flowing steam-producing water from said sample lines;
   filter means in each of said conduit means;
   a means defining a sample reservoir connected to each of said conduit means for the flow of steam-producing water from said sample lines thereinto;
   means defining and containing a supply of nitrogen and means for feeding said nitrogen to said sample reservoirs so that nitrogen is added thereto to cover the steam-producing water in said sample reservoirs;
   stirring means in each of said sample reservoirs for mixing the steam-producing water in said sample reservoirs;
   valve means in each of said conduit means for controlled flow of steam-producing water therethrough, said valve means including a first valve for controlling the flow of water into said conduit means and a metering valve for metering the flow of steam-producing water through said conduit means into said sample reservoirs;
   a plurality ion chromatographs for detecting the presence of selected corrosive impurities in the steam-producing water at said different points;
   means for selectively connecting any of said sample reservoirs to any one of said ion chromatographs for the flow of steam-producing water thereto;
   calibration means connectable in fluid communication with said ion chromatographs for calibrating said ion chromatographs, said calibration means including
   (i) a plurality of calibration reservoirs each containing a stock standard solution for calibrating a respective one of said ion chromatographs,
   (ii) means for selectively transferring any one of said stock standard solutions to a dilution reservoir,
   (iii) means for spraying water into said dilution reservoir for diluting said stock standard solution contained therein,
   (iv) means for stirring said stock standard solution and said water in said dilution reservoir, and
   (v) means for flowing said stock standard solution from said dilution reservoir to a selected one of said ion chromatographs; and
   control means for automatically controlling the operation of the on-line and continuous sampling of the steam-producing water, said ion chromatographs, and said calibration means.

2. The system of claim 1 including cooling means in each of said sample lines for reducing the temperature of the steam-producing water flowing therethrough.

3. The system of claim 1 wherein there are four ion chromatographs, a first one of said chromatographs to detect for the presence of inorganic anions, a second one of said chromatographs to detect for the presence of monovalent cations, a third one of said chromatographs to detect for the presence of divalent cations, and a fourth one of said chromatographs to detect for the presence of anions of organic acids.

4. The system of claim 1 wherein there are four calibration reservoirs each containing a stock standard solution for calibrating a respective one of said ion chromatographs.

5. A system for monitoring the ionic content of the steam-producing water in a steam-operated electrical generating power plant, comprising:
   a plurality of sample lines connectable in fluid communication with the steam-producing water at different points within the power plant;
   means for controlling the flow of steam-producing water through each of said sample lines for a predetermined period of time comprising a fill cycle;
   means defining a plurality of sample reservoirs, each of said sample lines connectable in fluid communication with a respective one of said sample reservoirs for the flow of steam-producing water thereinto during said fill cycle;
   a plurality of ion chromatographs for detecting for the presence of selected ions in the steam-producing water;
   selector valve means for flowing the steam-producing water from any one of said sample reservoirs to a selected one of said ion chromatographs so as to determine the ionic content of the steam-producing water at said different points over said predetermined period of time;
   means defining and containing a source of inert gas and means for feeding said inert gas to said sample reservoirs so that said inert gas is added thereto to cover the steam-producing water therein;

a plurality of calibration reservoirs each containing a stock standard solution for calibrating a respective one of said ion chromatographs prior to the initiation of a fill cycle;

means for diluting said stock standard solutions;

means for flowing a selected one of said diluted stock standard solutions to a respective one of said ion chromatographs; and control means for automatically controlling the flow of the steam-producing water and the stock standard solutions to said ion chromatographs.

6. The system of claim 5 wherein a conduit provides a fluid passageway between each of said sample lines and said sample reservoirs.

7. The system of claim 6 wherein each of said conduits contains a filter means for removing solids from the steam-producing water flowing therethrough.

8. The system of claim 7 wherein each of said conduits further includes a valve means for controlling the flow of steam-producing water thereinto and a metering valve for measuring the flow of steam-producing water into said sample reservoirs.

9. The system of claim 5 in which there are four of said ion chromatographs.

10. The system of claim 9 in which a first one of said ion chromatographs is used to detect inorganic anions, a second one of said ion chromatographs is used to detect monovalent cations, a third one of said ion chromatographs is used to detect divalent cations, and a fourth one of said ion chromatographs is used to detect ions of organic acids.

11. The system of claim 10 in which there are four calibration reservoirs each containing a separate stock standard solution for calibrating a respective one of said ion chromatographs.

12. A system for continuous sampling and on-line monitoring of the ionic content of the steam-producing water in an electrical generating power plant, comprising:

a plurality of sample lines for flowing steam-producing water from different points within the plant steam/water cycle;

valve means in each of said sample lines for controlling the flow of steam-producing water into said sample lines;

cooling means in each of said sample lines for reducing the temperature of the steam-producing water flowing therethrough;

conduit means connected to each of said sample lines for flowing the steam-producing water from said sample lines;

a means defining a sample reservoir in fluid communication with each of said conduit means for the flow of steam-producing water thereinto;

means defining and containing a source of inert gas and means for feeding said inert gas to said sample reservoirs so that said inert gas is added thereto to cover the steam-producing water therein;

valve means in each of said conduit means for controlled flow of the steam-producing water into said sample reservoirs over a predetermined period of time comprising a fill cycle;

a plurality of ion chromatographs for detecting the ionic content of the steam-producing water;

a first selector valve means and constant volume metering pump means for selectively flowing the steam-producing water from any one of said sample reservoirs to a selected one of said ion chromatographs so as to determine the ionic content of the steam-producing water at said different points during said fill cycle;

a plurality of calibration reservoirs each containing a stock standard solution for use in calibrating a respective one of said ion chromatographs;

means for diluting said stock standard solutions; and a second selector valve means and constant volume metering pump means for flowing a respective one of said diluted stock standard solutions to a selected one of said ion chromatographs.

13. The system of claim 12 wherein said first selector valve means and said constant volume metering pump means includes:

a first constant volume metering pump for injecting steam-producing water in said sample reservoirs into said ion chromatographs;

a first selector valve for placing said first pump and a selected one of said sample reservoirs in fluid communication; and a second selector valve for placing said pump and a selected one of said ion chromatographs in fluid communication.

14. The system of claim 13 wherein said dilution means comprises:

a dilution reservoir;

a second constant volume metering pump for flowing said stock standard solutions from said calibration reservoirs to said dilution reservoir;

a third selector valve for placing said dilution reservoir and a selected one of said calibration reservoirs in fluid communication;

a third constant volume metering pump for flowing water to said dilution reservoir;

means for spraying the water into said dilution reservoir; and stirrer means for mixing the water and said stock standard solution in said reservoir.

15. The system of claim 14 wherein said means for flowing a respective one of said diluted stock standard solution to a selected one of said ion chromatographs includes said first selector valve and said first pump.

* * * * *

UNITED STATES PATENT AND TRADEMARK OFFICE
CERTIFICATE OF CORRECTION

PATENT NO. : 4,472,354

DATED : September 18, 1984

INVENTOR(S) : Passell, et al.

It is certified that error appears in the above-identified patent and that said Letters Patent are hereby corrected as shown below:

At Column 1, line 16, the word "concentation" should be --concentration--.

At Column 1, line 18, the word "vaprozied" should be --vaporized--.

At Column 1, line 24, the word "one" should be --once--.

At Column 1, line 52, the name "Hickman" should be --Hickam--.

At Column 5, line 39, the word "present" should be --presence--.

Signed and Sealed this

Fifteenth Day of October 1985

[SEAL]

Attest:

*Attesting Officer*

DONALD J. QUIGG

*Commissioner of Patents and Trademarks—Designate*